United States Patent [19]

Bowen

[11] 4,180,065
[45] Dec. 25, 1979

[54] ANTI-EMBOLISM STOCKING

[75] Inventor: Omer J. Bowen, Fayetteville, Ak.

[73] Assignee: Bear Brand Hosiery Co., Chicago, Ill.

[21] Appl. No.: 871,181

[22] Filed: Jan. 23, 1978

[51] Int. Cl.² .............................................. A61F 13/00
[52] U.S. Cl. ......................................... 128/165; 2/239; 66/172 E
[58] Field of Search .................... 128/165; 2/239–241; 66/172 E, 178 R, 178 A

[56] References Cited

U.S. PATENT DOCUMENTS

| | | | |
|---|---|---|---|
| 2,445,049 | 7/1948 | Welch | 2/239 |
| 2,574,873 | 11/1951 | Jobst | 128/165 |
| 3,728,875 | 4/1973 | Hartigan et al. | 66/172 E |
| 3,975,929 | 8/1976 | Fregeolle | 66/172 E |
| 3,983,870 | 10/1976 | Herbert et al. | 128/165 |
| 4,027,667 | 6/1977 | Swallow et al. | 128/165 |
| 4,048,818 | 9/1977 | Cueman | 66/178 A |

*Primary Examiner*—Robert E. Bagwill
*Attorney, Agent, or Firm*—Vogel, Dithmar, Stotland, Stratman & Levy

[57] ABSTRACT

A one-piece seamless unidirectional rotary knitted anti-embolism stocking comprises a seamless tubular body integrally knitted and having varying lengths of yarn in the courses thereof resulting in a varying cross section such that the circumferential tension of the stocking decreases from the toe end to the upper end thereof. Specifically, constant cross section portions are interconnected by transition portions of gradually varying cross section in a pattern to produce on the wearer's leg a pressure which decreases substantially uniformly from the ball of the foot to the top of the stocking. Each end of the tubular body has a two-ply welt portion, and a heel patch is inlaid in the foot portion of the tubular body. The toe end of the tubular body terminates in a toe portion which is folded back on itself and seamed at the side edges of the fold. In one embodiment the toe portion is cut away along one-half the circumference and length thereof to leave a flap which is folded back and seamed to form a reduced thickness toe. Knee-high and thigh-high embodiments of the stocking are disclosed along with methods of making same on an eight-feed circular knitting machine.

9 Claims, 16 Drawing Figures

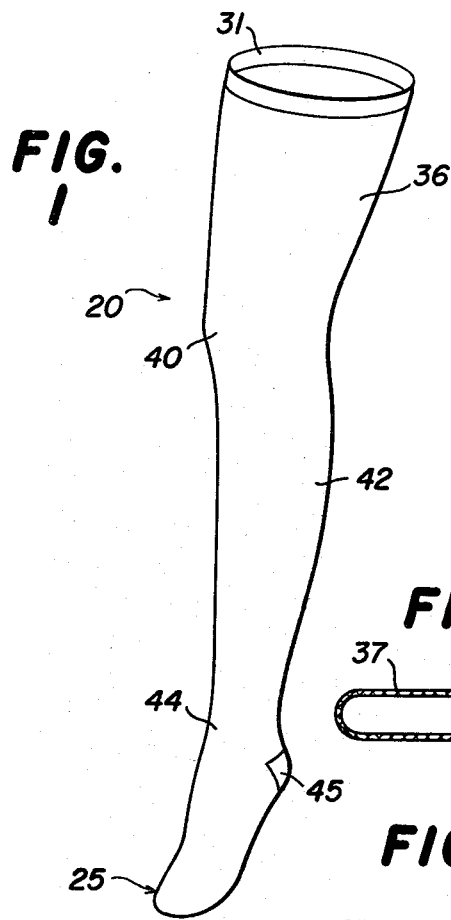
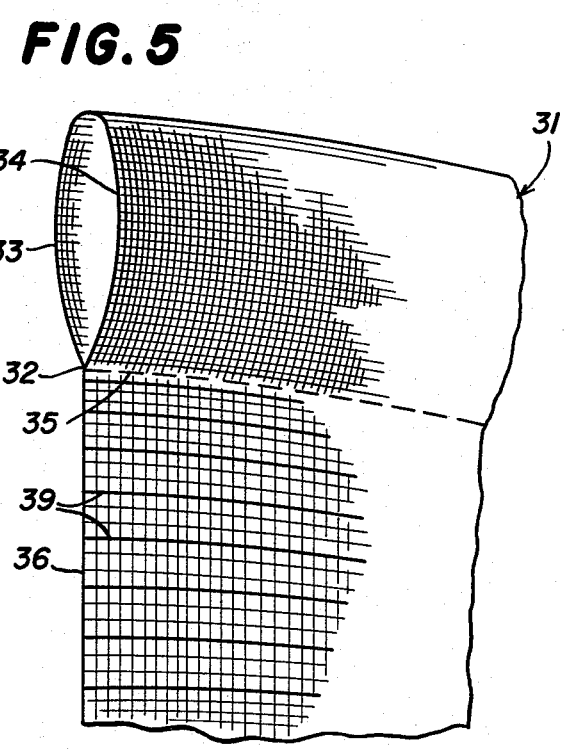
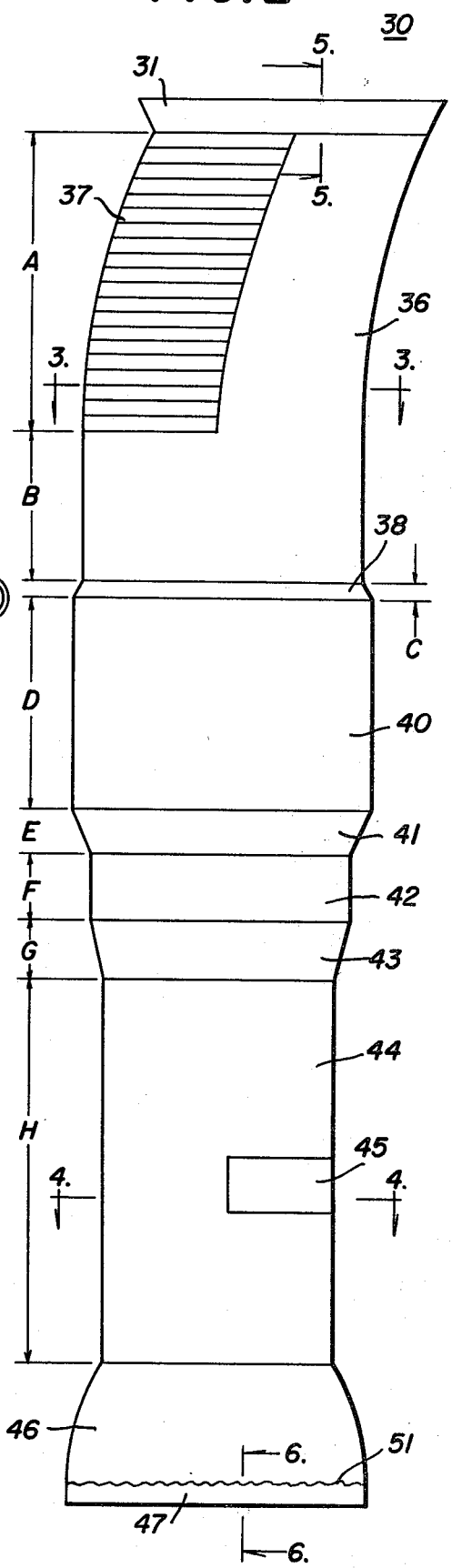

ANTI-EMBOLISM STOCKING

BACKGROUND OF THE INVENTION AND PRIOR ART STATEMENT

The present invention relates to leg-compressing or anti-embolism stockings.

It is known that it is desirable for various medical purposes to apply pressure to a patient's leg in order to control the blood supply of the vascular system in the leg. For example, blood may tend to pool in the vessels of a patient's feet, and it is desirable to inhibit this pooling and force the blood to a more even distribution over the patient's legs. For this purpose it is usually desirable, to achieve optimum results, that a pressure be exerted on the leg which decreases from the foot to the top of the leg. The desired pressure application can be achieved by wrapping elastic bandages around the legs, but this requires application by skilled personnel and can be quite time-consuming, and bandages tend to slip on the leg, resulting in undesirable shifting of the pressure distribution and the leaving of constriction wrinkles on the user's leg.

In order to avoid these disadvantages, elastic stockings have been developed. While such stockings are much easier to use than elastic bandages, there has not been developed a stocking which achieves the desired pressure distribution on the leg, with the pressure decreasing from the ball of the foot to the upper end of the stocking.

One such elastic stocking is disclosed in British Patent No. 1,445,233, the complete specification of which was published on Aug. 4, 1976. That patent discloses a rotary knitted integral one-piece stocking in which there are variations in the circumferential tension along the length of the stocking tube. But in that stocking the tension is greatest at the calf portion of the stocking, the tension decreasing from there toward the thigh portion and toward the foot portion of the stocking. A copy of that prior patent is filed herewith.

Other stockings achieve a pressure decrease which begins at the wearer's ankle and thus does not solve the problem of pooling of blood in the feet.

SUMMARY OF THE INVENTION

The present invention relates to an improved elastic anti-embolism stocking, and it is a general object of this invention to provide an anti-embolism stocking which achieves the desired pressure distribution on the wearer's leg, with the pressure gradually decreasing from the ball of the wearer's foot to the top of the stocking.

More particularly, it is an important object of this invention to provide a stocking of the type set forth which is of rotary knitted one-piece construction, comprising a seamless tubular body having a cross section which increases in stages from the foot end to the boot end thereof.

It is another object of this invention to provide a stocking of the type set forth, which includes transition portions between constant cross section portions, with each transition portion including a plurality of courses of progressively increasing or decreasing cross section.

Another object of this invention is to provide a stocking of the type set forth which has a closed toe formed by folding over the distal end of the tubular body.

It is another object of this invention to provide a stocking of the type set forth in both knee-high and full-length versions, with the full-length version having an enlarged cross section knee portion to accommodate flexing of the wearer's knee.

Another object of this invention is the provision of a stocking of the type set forth which includes an inlaid heel patch positioned to provide reinforcement at the area of the stocking engaged by the wearer's heel in use.

In summary, these objects are attained in the present invention by the provision of a rotary knitted one-piece anti-embolism stocking comprising a seamless tubular body integrally knitted with at least certain of the courses therein of elastomeric yarn so as to impart an elastic character to the body, the body including a foot portion and a boot portion connected to the foot portion, the foot portion having a toe end disposable in use at the ball of the wearer's foot and the boot portion having an upper end disposed away from the foot portion, the tubular body having a cross section which varies such that in use on a wearer's leg the tubular body has a circumferential tension which decreases essentially uniformly from the toe end of the foot portion to the upper end of the boot portion, whereby the stocking applies to a wearer's leg a pressure which decreases essentially uniformly from the ball of the wearer's foot to the top of the stocking.

Further features of the invention pertain to the particular arrangement of the parts of the anti-embolism stocking whereby the above-outlined and additionafeatures thereof are attained.

The invention, both as to its organization and method of operation, together with further objects and advantages thereof, will best be understood by reference to the following specification taken in connection with the accompanying drawings.

BRIEF DESCRIPTION OF THE DRAWINGS

FIG. 1 is a perspective view of a first embodiment of a one-piece seamless stocking made in accordance with and embodying the principles of the present invention, the stocking being illustrated in the shape it would assume in position on a wearer's leg;

FIG. 2 is an elevational view of the greige blank for the stocking of FIG. 1 before formation of the toe;

FIG. 3 is a view in horizontal section taken along the line 3—3 in FIG. 2;

FIG. 4 is a view in horizontal section taken along the line 4—4 in FIG. 2;

FIG. 5 is a further enlarged fragmentary view in cross section taken along the line 5—5 in FIG. 2;

DESCRIPTION OF THE PREFERRED EMBODIMENTS

Figure 6:
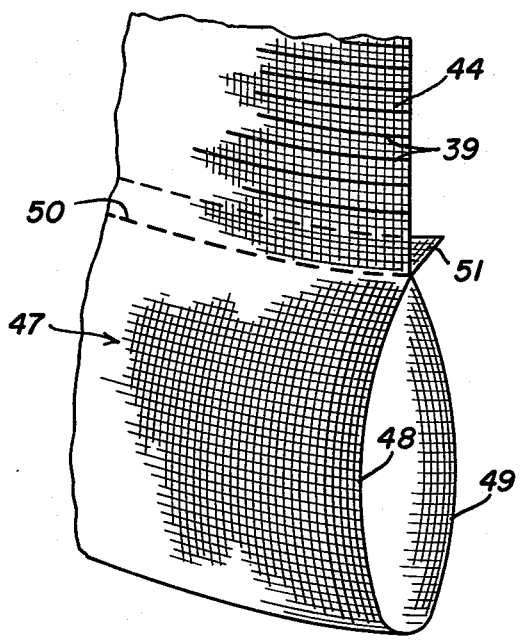
FIG. 6 is an enlarged fragmentary view in vertical section taken along the line 6—6 in FIG. 2.
Figure 7:
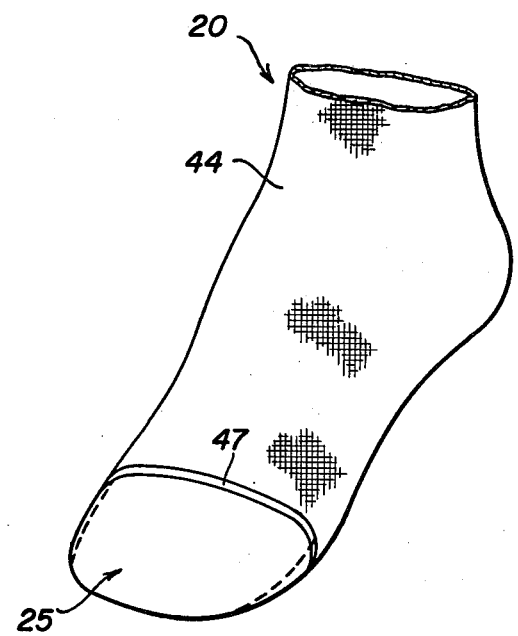
FIG. 7 is an enlarged fragmentary perspective view of the foot portion of the stocking of FIG. 1.
Figure 8:
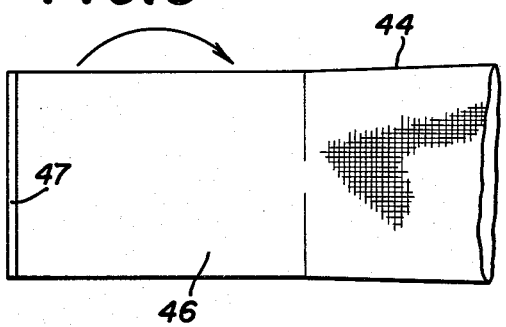
FIG. 8 is a reduced fragmentary elevational view of the lower end of the greige blank of FIG. 2, rotated 90 degrees, and illustrating a first step in the formation of the toe of the stocking.

Referring to FIGS. 1 through 7 of the drawings, there is illustrated a first embodiment of a one-piece seamless stocking 20 made in accordance with and embodying the principles of the present invention, the stocking 20 being a full-leg or thigh-high stocking having a closed toe, generally designated by the numeral 25.

Referring to FIG. 2, there is illustrated the greige blank for the stocking 20, which comprises a tubular body, generally designated by the numeral 30, which includes an upper leg welt band 31, an upper boot or thigh portion 36 having a relief panel 37 formed therein, a transition portion 38, a knee portion 40, a transition portion 41, a calf portion 42, a transition portion 43, a foot portion 44 having a heel patch 45 formed therein and a toe portion 46 provided with a toe welt band 47 at the distal end thereof. The stocking 20 is knit as a single continuous seamless tube using a unidirectional rotary knitting method and is continually knit starting with the welt band 31 and proceeding to the welt band 47 in a continuous uninterrupted manner.

Referring to FIG. 5, the details of construction of the welt band 31 are shown. The stocking 20 actually is knitted beginning at the make-up 32. Integral with the make-up 32 is an inside band portion 33 that is integral with an outside band portion 34, the band portions 33 and 34 being joined at the juncture 35, as will be described more fully hereinafter, to provide the completed welt band 31.

The stocking 20 is preferably knit upon an eight-feed rotary knitting machine such as an eight-feed "Zodiac" machine manufactured by the Billi Company of Italy. In one preferred form of such machine, 400 or more knitting needles are provided as well as a dial for make-up. The following is a description of the knitting of the stocking 100 using such an eight-feed machine.

The welt band 31 is knit as described above, using six of the machine's eight feeds (preferably feeds 1, 3, 4, 5, 7 and 8), with all six feeds feeding a stretch yarn and knitting on all 400 needles.

Beginning with the first course of the thigh portion 36 at the juncture 35, and continuing throughout the tubular body 30 until the last course of the toe portion 46 at the juncture 55, feeds 4 and 8 continue knitting on 400 needles, while feeds 1, 3, 5 and 7 are knitting on only 200 needles, i.e., alternate ones of the needles are held down as the cylinder turns through feeds 1, 3, 5 and 7. In addition, throughout the tubular body 30 from the first course of the thigh portion 36 to the last course of the foot portion 44, an elastomeric yarn is fed instead of the stretch yarn on feeds 1 and 5, the elastomeric yarn preferably being knit at six grams of tension. This tension on the elastomeric yarn feeds, together with the reduced number of needles knitting on four of the six feeds, results in a tighter knit and consequently increased tension in the thigh portion 36, knee portion 40, foot portion 44 and transition portions 38, 41 and 43, as compared with the welt band 31.

The relief panel 37 is formed by part-coursing. More particularly, for a predetermined number of courses corresponding to the desired longitudinal extent of the relief panel 37, feed 2 is dropped in for about one-half of the fabric circumference, feeding a stretch yarn and knitting on 400 needles. To form the heel patch 45, an additional heavier weight stretch yarn is fed to feed 4 in addition to the stretch yarn already being fed thereby, for the desired longitudinal and circumferential extent of the heel patch 45.

It is an important feature of the present invention that the cross-sectional dimensions of the tubular body 30 are varied along the length thereof in a manner such as to achieve a substantially uniform decrease in circumferential tension from the toe end of the foot portion 44 to the upper end of the thigh portion 36. This variation in cross-sectional dimension is achieved by the use of a graduator cam, which may be of the type illustrated in FIG. 15, and generally designated by the numeral 90. The cam 90 controls the height of the needles with respect to the sinkers of the knitting machine, thereby to control the length of yarn drawn by the needles in each course of the stocking 20. The greater the length of yarn drawn in each course, the greater will be the circumference or perimeter of that course and the less will be the circumferential tension thereof.

Figure 15:
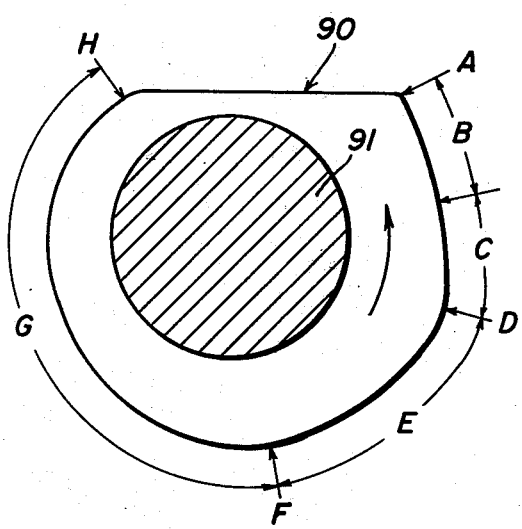
FIG. 15 is a cross-sectional view of a knitting machine cam shaft illustrating in elevation a graduator cam for controlling the graduation of the cross section of the greige blank of FIG. 2 during the knitting thereof.

More particularly, referring to FIGS. 2 and 15 of the drawings, the welt band 31 is formed under the control of a welt sizing cam. At the beginning of the thigh portion 36, the graduator cam 90 comes into play, the cam 90 being rotatably mounted on a shaft 91. Throughout the upper portion of the thigh portion 36 corresponding to the relief panel 37, designated A, the graduator cam 90 is stationary at the position A for holding the needles at a fixed height and drawing a fixed length of yarn for each course. At the course corresponding to the lower end of the relief panel 37, the graduator cam 90 moves in the direction indicated by the arrow in FIG. 15, resulting in a slight variation in the height of the needles to slightly reduce the length of yarn drawn thereby in each course, and thereby increase the circumferential tension in the lower part of the thigh portion 36, designated B. Beginning with the course corresponding to the lower end of the thigh portion 36, the graduator cam 90 continues moving, varying the height of the needles in the opposite direction to increase the length of yarn drawn thereby and gradually decrease the circumferential tension in each course of the transition portion 38, designated C.

When the graduator cam 90 reaches the position D, it remains stationary throughout the knee portion 40, and at the course corresponding to the last course of the knee portion 40, the graduator cam 90 resumes moving from position D, thereby again varying the height of the needles to gradually draw less yarn throughout the transition portion 41, designated E, to gradually increase the circumferential tension of the courses of the transition portion 41. When the graduator cam 90 reaches the position F, it again remains stationary throughout the calf portion 42, and then resumes movement during the knitting of the transition portion 43, designated G, during which portion the height of the needles is again varied to decrease the amount of yarn drawn during each course until the position H is reached. The graduator cam 90 remains stationary at the position H during the knitting of the foot portion 44. The knitting of the toe portion 46 is controlled by a separate toe sizing cam.

A measure of the graduated cross section and graduated circumferential tension of the tubular body 30 is the cross stretch thereof. In the preferred embodiment, tubular body 30 has a cross stretch of 11½ inches in the upper part A of the thigh portion 36, 11 inches in the lower part B of the thigh portion 36, 11½ inches in the knee portion 40, 10 inches in the calf portion 42, and 8 inches in the foot portion 44. It will, therefore, be appreciated that, with the exception of the knee portion 40, the tubular body 30 has a cross stretch which increases and a corresponding circumferential tension which gradually decreases from the toe end of the foot portion 44 to the upper end of the thigh portion 36. In use, the toe end of the foot portion 44 will be disposed approximately at the ball of the wearer's foot, the graduation of the cross section of the tubular body 30 being so designed that the stocking 20 applies to the wearer's leg a pressure which substantially uniformly decreases from the ball of the wearer's foot to the top of the stocking. In this regard, it will be noted that the slightly increased cross section of the knee portion 40 as compared to the lower part B of the thigh portion 36 serves to afford this continuous and substantially uniform decrease in pressure, while at the same time accommodating flexing of the wearer's knee.

In the knitting of the toe portion 46, the elastomeric yarn is removed from feeds 5 and 7 and is replaced by the same type of stretch yarn as is being fed on the other feeds. At the distal end of the toe portion 46 the welt band 47 is formed. For this purpose, feed 8 is taken out of action, leaving five feeds remaining in action, and the needles on feed 4 are held down while knitting continues on feeds 1, 3, 5 and 7. Referring to FIG. 6, there is first formed an outside band portion 48 that is in turn integral with an inside band portion 49, the band portions 48 and 49 being knit together as at the juncture 50. The needles are held down at feed 4 until the desired double welt length is reached, and then the needles are again raised to knitting height, thereby creating a small turned welt. Also integral with the juncture 50 is a selvage or runoff 51, which is the last portion of the stocking 20 to be knitted. For the runoff 51, all feeds are taken out of action except feed 4, which knits a stretch yarn plus a lower melting point yarn for four or five courses which will fuse at the dyebath temperature to prevent raveling of the fabric at the runoff 51. In addition, the tubular body 30 is boarded at a temperature of approximately 265° F., as opposed to the more normal boarding temperature of 250°–252° F. This elevated boarding temperature serves to increase the nylon shrinkage and help reduce the overall cross-sectional dimensions of the tubular body 30 to achieve a proportionately higher circumferential tension thereof.

Figure 9:
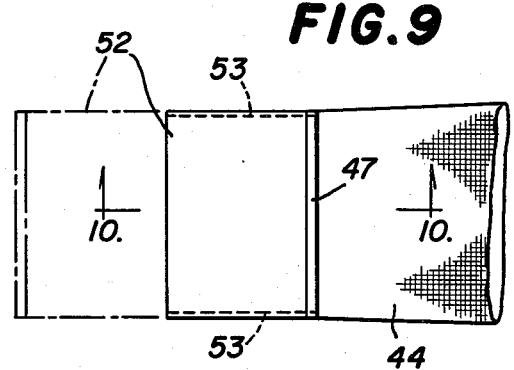
FIG. 9 is a view similar to FIG. 8, illustrating the completed toe of the stocking in a closed configuration.
Figure 10:
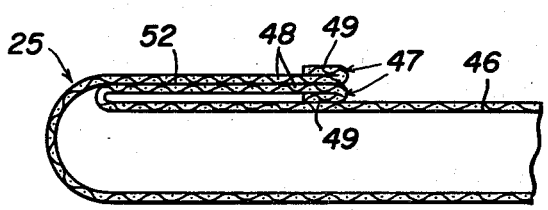
FIG. 10 is an enlarged fragmentary view in cross section taken along the line 10—10 in FIG. 9.

Referring now to FIGS. 8 through 11 of the drawings, after dyeing and boarding, the toe 25 of the stocking 20 is formed. For this purpose, the tubular body 30 is laid flat, and the toe portion 46 is folded in half back upon itself, as indicated by the arrow in FIG. 8, the distal half of the toe portion 46 forming a flap 52 which, after folding, overlaps the other half of the toe portion 46, the overlapping portions then being seamed together along the sides thereof as at 53 (see FIG. 9), longitudinally of the tubular body 30, thereby closing the toe end of the tubular body 30 to form the toe 25, as indicated in FIG. 10.

It is an important feature of this invention that this unique construction of the toe 25 permits it to be selectively used in either an open-toe or a closed-toe configuration. More particularly, for changing the toe 25 to the open-toe configuration, the outer layer of the flap 52 is folded 180 degrees back over the end of the toe 25 to overlap the opposite side of the toe portion 46, this folding motion being indicated in FIG. 11. It will be appreciated that when thus folded, the flap 52 will form an outturned cuff or hem around the entire circumference of the foot portion 46, thereby opening the end thereof.

Figure 11:
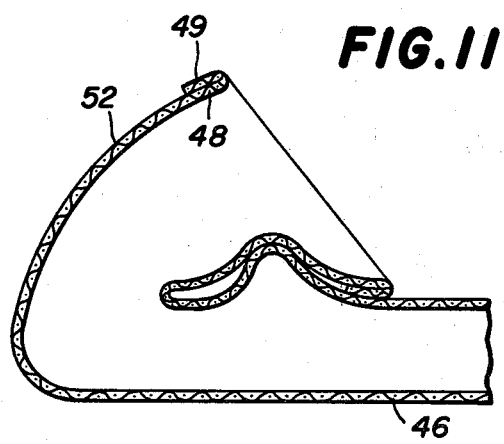
FIG. 11 is an enlarged fragmentary cross-sectional view similar to FIG. 10, and illustrating the folding of the toe portion of the stocking from the configuration illustrated in FIG. 10 to an open-toe configuration.
Figure 12:
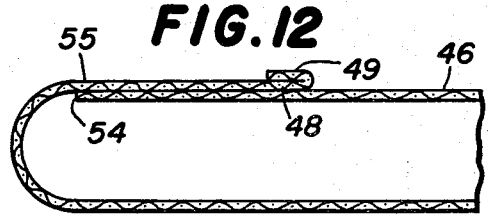
FIG. 12 is a view similar to FIG. 10 and illustrating a second embodiment of the toe portion of the stocking.

Since the embodiment of FIGS. 9 through 11, in the closed-toe configuration thereof, results in three thicknesses of material along the top of the wearer's toes, this arrangement may in some cases cause an uncomfortably snug fit inside a wearer's shoe. Therefore, an alternative embodiment of the toe 25 is provided, as illustrated in FIG. 12. In this embodiment, after the tubular body 30 is laid flat, the toe portion 46 is slit from the distal end thereof along the opposite sides thereof to about midway along the longitudinal extent thereof, thereby forming two flaps, one of which is then cut off, as at 54. The remaining flap is then folded back along the outside of the adjacent toe portion 46 and seamed thereto along the opposite sides thereof, resulting in an open-toe configuration. For conversion to the closed-toe configuration, this flap is simply turned back 180 degrees over the distal end of the toe portion 46 to the position illustrated in FIG. 12, where it overlies the cut end of the toe portion 46, thereby closing the toe 25. In this embodiment there are no more than two thicknesses of material in either the open-toe or closed-toe configuration.

The stretch yarn used in the knitting of the stocking 20 is made from thermoplastic fiber or fibers, usually in continuous filament form, which is capable of a pronounced degree of elongation and a rapid recovery, this property being obtained by having the yarn subjected to an appropriate combination of deforming, heat setting and developing treatments, this including crimp yarn, torque yarn and non-torque yarn. Suitable materials for such stretch yarn are nylon, polypropylene and polyester resins. Such yarn may be from 30 denier to 70 denier and may comprise a plurality of filaments, the yarn preferably being of the S and Z twist type. A preferred yarn is 2/30 plied S and Z nylon which is used in all of the non-elastomeric courses of the tubular body 30. The additional stretch yarn which is fed on feed 4 in the heel patch 45 is preferably a 2/70 plied S and Z nylon.

An elastomeric yarn is a yarn made from an elastic material such as polyurethane or rubber. Such yarn is also preferably single wrapped or double wrapped with nylon of 20 to 40 denier and containing 7 to 13 filaments. A preferred elastomeric yarn is that manufactured by Macfield Company—Style G-140-58, which comprises a core of 265 denier elastomeric yarn sold under the trademark "GloSpan", a top cover of 20 denier 7 filament nylon, and an inner cover of 20 denier 7 filament nylon. This elastomeric yarn has an elongation of 352 percent and a yield of 10,432 yards per pound.

The stocking 20 may be made in a variety of sizes having different lengths and cross sections. Typical course counts for the boot and foot of several such sizes are set forth in TABLE I below, wherein the "boot" comprises the portions A–G in FIG. 2, while the "foot" comprises the portion H in FIG. 2.

TABLE I

|   |      | Short | Medium | Long |
|---|------|-------|--------|------|
| A | Boot | 2280  | 2328   | 2376 |
|   | Foot | 396   | 396    | 396  |
| B | Boot | 2328  | 2376   | 2424 |
|   | Foot | 444   | 444    | 444  |
| C | Boot | 2376  | 2424   | 2472 |
|   | Foot | 492   | 492    | 492  |

From the foregoing, it can be seen that the stocking 20 affords a substantially uniform decrease in pressure applied to the wearer's leg, from the ball of the wearer's foot to the top of the stocking, while at the same time permitting flexing of the wearer's knee. This pressure distribution results from the unique graduation of the cross-sectional dimensions of the stocking 20 by uniquely controlling the length of yarn in each of the courses. The cross-sectional dimensions of the tubular body 30 are also affected by the feeding of the elastomeric yarns at a predetermined tension and by the boarding of the finished greige blank at a predetermined elevated temperature to increase shrinkage of the nylon.

Furthermore, the use of a different number of feeds and different numbers of needles at various portions of the stocking 20 also affect the cross-sectional dimensions and circumferential tension thereof. More particularly, the use of 400 needles in all feeds of the welt bands 31 and 47 results in a relatively loose knit in these welt bands as compared to the knit in the remainder of the stocking 20 in which four of the feeds are knitting on only 200 needles. In this regard it is noted that since 400 needles are used in the welt bands 31 and 47, at least one 400 needle feed is maintained throughout the rest of the tubular body 30 in order to prevent laddering of the stitches in the material when the shift is made to 200 needles. The use of 400 needles in the welt bands 31 and 47, in addition to providing a looser knit in these portions, also has been found to result in an improved toe welt 47 and improved runoff therefrom.

Figure 13:
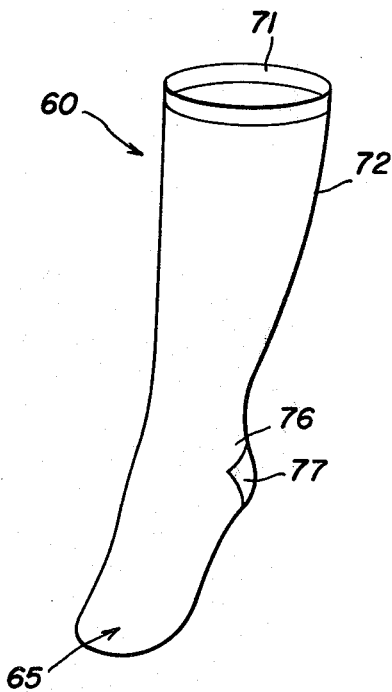
FIG. 13 is a perspective view similar to FIG. 1, and illustrating a second embodiment of the stocking of the present invention.
Figure 14:
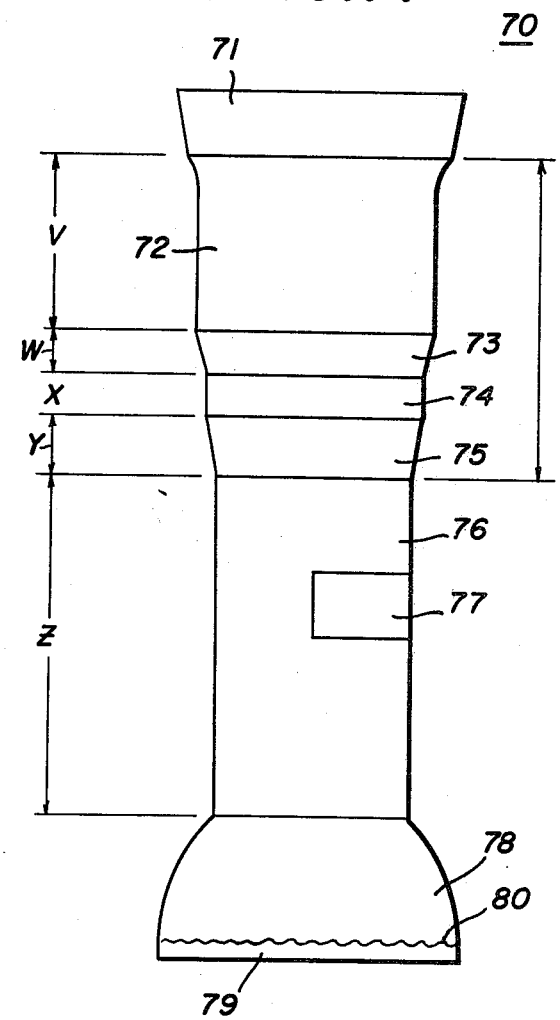
FIG. 14 is an enlarged elevational view of the greige blank for the stocking of FIG. 13 before formation of the toe thereof.

Referring now to FIGS. 13 and 14 of the drawings, there is illustrated a second embodiment of stocking constructed in accordance with the present invention, generally designated by the numeral 60, the stocking 60 being a knee-high stocking having a closed toe, generally designated by the numeral 65.

Referring to FIG. 4, there is illustrated the greige blank for the stocking 60, which comprises a tubular body, generally designated by the numeral 70, which includes an upper leg welt band 71, an upper boot or calf portion 72, a transition portion 73, an ankle portion 74, a transition portion 75, a foot portion 76 having a heel patch 77 formed therein and a toe portion 78 provided with a toe welt band 79 at the distal end thereof. The stocking 60 is knit as a single continuous seamless tube using a unidirectional rotary knitting method and is knit starting with the welt band 71 and processing to the welt band 79 in a continuous uninterrupted manner.

The welt bands 71 and 79 are two-ply turned welts and are formed in essentially the same manner as the welt bands 31 and 47, as described above in connection with FIGS. 5 and 6, the stocking 60 preferably being knit on the same type of rotary knitting machine as was referred to above in connection with the knitting of the stocking 20. However, in knitting the stocking 60, only five of the machine's eight feeds (preferably feeds 1, 3, 4, 5 and 7) are used.

In knitting the two-ply welt band 71, all five feeds feed a stretch yarn and knit on all 400 needles. Beginning with the first course of the upper calf portion 72, and continuing throughout the tubular body 70 until the last course of the toe portion 78, feed 4 continues knitting on 400 needles, while feeds 1, 3, 5 and 7 are knitting on only 200 needles, i.e., alternate ones of the needles are held down while the cylinder turns through feeds 1, 3, 5 and 7. In addition, throughout the tubular body 70 from the first course of the upper calf portion 72 to the last course of the foot portion 76, an elastomeric yarn is fed instead of the stretch yarn on feed 1, the elastomeric yarn preferably being knit at fourteen grams of tension. This tension on the elastomeric yarn feed, together with the reduced number of needles knitting on four of the five seeds, results in a tighter knit and, consequently, increased tension in the upper and lower calf portions 72 and 74, transition portions 73 and 75 and foot portion 76, as compared with the welt band 71.

To form the heel patch 77, an additional heavier weight stretch yarn is fed to feed 4 in addition to the stretch yarn already being fed thereby, for the desired longitudinal and circumferential extent of the heel patch 77.

It is an important feature of the invention that the cross-sectional dimensions of the tubular body 70 are varied along the length thereof in a manner such as to achieve a substantially uniform decrease in circumferential tension from the toe end of the foot portion 76 to the upper end of the upper calf portion 72. This variation in cross-sectional dimension is achieved by the use of a graduator cam, which may be of the type illustrated in FIG. 16, and is generally designated by the numeral 95. The graduator cam 95 controls the height of the needles with respect to the sinkers of the knitting machine, thereby to control the length of yarn drawn by the needles in each course of the stocking 60, as was described above in connection with the stocking 20.

Figure 16:
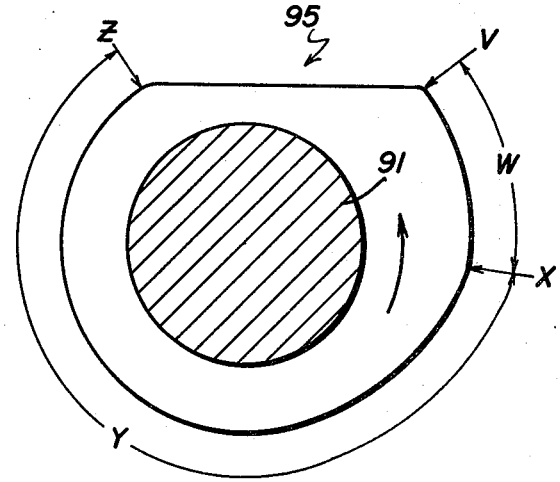
FIG. 16 is a view similar to FIG. 15, illustrating a graduator cam for controlling the graduation of the cross section of the greige blank of FIG. 14 during the knitting thereof.

More particularly, referring to FIGS. 14 and 16 of the drawings, the welt band 71 is formed under the control of a welt sizing cam. At the beginning of the upper calf portion 72, designated V, the graduator cam 95 comes into play, the cam 95 being rotatably mounted on the shaft 91. Throughout the portion V the graduator cam 95 is stationary at the position designated V for holding the needles at a fixed height and drawing a fixed length of yarn for each course, whereby the cross section of the tubular body 70 remains constant throughout the upper calf portion 72. At the course corresponding to the lower end of the upper calf portion 72, the graduator cam 95 moves from position V in the direction indicated by the arrow in FIG. 16, resulting in a slight variation in the height of the needles gradually to reduce the length of yarn drawn thereby in each course and correspondingly increase the circumferential tension for knitting the transition portion 73, designated W. When the graduator cam 95 reaches the position X, it remains stationary throughout the lower calf portion 74, and then resumes movement during the knitting of the transition portion 75, designated Y, during which portion the height of the needles is again varied to decrease the amount of yarn drawn during each course until the position Z is reached. The graduator cam 95 remains stationary at the position Z during the knitting of the foot portion 76.

The knitting of the toe portion 78 is controlled by a separate toe sizing cam. During knitting of the toe portion 78, the elastomeric yarn in feed 1 is replaced by the same type of stretch yarn as is fed in the other feeds. At the distal end of the toe portion 78, the welt band 79 is formed. For this purpose, the stitches are held on feed 4 with the needles down, while knitting continues on feeds 1, 3, 5 and 7 until the desired length of welt is formed, and then the needles on feed 4 are again raised to knitting height, thereby creating a small turned welt, as described above. Also integral with the welt band 79 at the end thereof is a selvage or runoff 80, which is the last portion of the stocking 60 to be knitted. For the runoff 80, all feeds are taken out of action except feed 4, which knits a stretch yarn plus a lower melting point yarn which will fuse at the dyebath temperature to prevent raveling of the fabric at the runoff 80. Boarding may then be performed in the same manner as was described above in connection with the stocking 20.

A measure of the graduated cross section and graduated circumferential tension of the tubular body 70 is the cross stretch thereof. Preferably the tubular body 70 has a cross stretch of 9½ inches in the upper calf portion 72, 8 inches in the lower calf portion 74 and 7 inches in the foot portion 76. It will, therefore, be appreciated that the tubular body 70 has a cross stretch which increases and a corresponding circumferential tension which gradually decreases from the toe end of the foot portion 76 to the upper end of the upper thigh portion 72. In use, the toe end of the foot portion 76 will be disposed approximately at the ball of the wearer's foot, the graduation of the cross section of the tubular body 70 being so designated that the stocking 60 applies to the wearer's leg a pressure which substantially uniformly decreases from the ball of the wearer's foot to the top of the stocking.

After dyeing and boarding, the toe 65 of the stocking 60 is formed in the same manner as was described above in connection with FIGS. 8 through 12 for the stocking 20. Thus, either the double thickness or triple thickness type toe may be formed, either type being foldable between open-toe and closed-toe configurations.

Preferably, the stretch yarn used in all of the non-elastomeric courses of the stocking 20 is a 2/30 plied S and Z nylon, while the additional stretch yarn fed at feed 4 for the heel patch 77 is a 2/70 plied S and Z nylon. The elastomeric yarn fed in feed 1 throughout the portions of the tubular body 70 designated V-Z is preferably of the type manufactured by TexElastic Corp.—Style 4013 having a core of 466 denier elastomeric yarn of the type sold under the trademark "GloSpan", a top cover of 20 denier 7 filament nylon and an inner cover of 20 denier 7 filament nylon, this elastomeric yarn having an elongation of 345 percent and a yield of 7600 yards per pound.

The stocking 60 is preferably provided in a variety of sizes having different lengths and cross sections, the course counts for the boot and foot of typical ones of these sizes being set forth in TABLE II below, wherein the "boot" comprises the portions designated V-Y in FIG. 14, and the "foot" comprises the portion designated Z in FIG. 14.

TABLE II

|   |   | Medium | Long |
|---|---|---|---|
| A | Boot | 1080 | 1120 |
|   | Foot | 550 | 550 |
| B | Boot | 1120 | 1160 |
|   | Foot | 600 | 600 |
| C | Boot | 1160 | 1200 |
|   | Foot | 650 | 650 |
| D | Boot | 1240 | 1300 |
|   | Foot | 690 | 690 |

While there have been described what are at present considered to be the preferred embodiments of the invention, it will be understood that various modifications may be made therein, and it is intended to cover in the appended claims all such modifications as fall within the true spirit and scope of the invention.

What is claimed is:

1. A rotary knitted one-piece anti-embolism stocking comprising a seamless tubular body integrally knitted with at least certain of the courses therein of elastomeric yarn so as to impart an elastic character to said body, said body including a foot portion and a calf portion and a knee portion and a lower thigh portion and an upper thigh portion, said body further including first and second transition portions connecting said calf portion respectively to said foot portion and said knee portion and a third transition portion connecting said knee portion to said lower thigh portion, said foot portion having a toe end disposable in use at the ball of the wearer's foot and said thigh portion having an upper end disposed away from said knee portion, said calf portion having a cross section greater than the cross section of said foot portion and less than the cross section of said lower thigh portion and said knee portion having a cross section greater than the cross section of said lower thigh portion and substantially equal to the cross section of said upper thigh portion, said first transition portion having a cross section which increases gradually from said foot portion to said calf portion and said second transition portion having a cross section which increases gradually from said calf portion to said knee portion and said third transition portion having a cross section which decreases gradually from said knee portion to said lower thigh portion, the variation in the cross section of said tubular body being such that in use on a wearer's leg said tubular body has a circumferential tension which decreases essentially uniformly from said toe end of said foot portion to said upper end of said thigh portion while said enlarged knee portion accommodates flexing of the wearer's knee, whereby said stocking applies to a wearer's leg a pressure which decreases essentially uniformly from the ball of the wearer's foot to the upper portion of the wearer's thigh.

2. The stocking set forth in claim 1, and further including a relief panel integrally knit in said thigh portion of said tubular body along approximately one-half the circumference thereof and disposable along the inside of a wearer's thigh.

3. The stocking set forth in claim 1, wherein said upper end of said thigh portion has integrally knitted thereon a seamless welt band turned upon itself and integrally knitted with itself to provide a double thickness.

4. A rotary knitted one-piece anti-embolism stocking comprising a seamless tubular body integrally knitted with at least certain of the courses therein of elastomeric yarn so as to impart an elastic character to said body, said body including a foot portion and a calf portion and a knee portion and a lower thigh portion and an upper thigh portion, said body further including first and second transition portions connecting said calf portion respectively to said foot portion and said knee portion and a third transition portion connecting said knee portion to said lower thigh portion, said foot portion having a toe end disposable in use at the ball of the wearer's foot and said thigh portion having an upper end disposed away from said knee portion, each of the courses in said foot portion having a first predetermined length of yarn therein and each of the courses in said calf portion having a second predetermined length of yarn therein greater than said first predetermined length and each of the courses in said lower thigh portion having a third predetermined length of yarn therein greater than said second predetermined length and each of the courses in said upper thigh portion and said knee portion having a fourth predetermined length of yarn therein greater than said third predetermined length, the courses of said first transition portion having lengths of yarn therein which increase gradually from said first predetermined length at said foot portion to said second predetermined length at said calf portion, the courses in said second transition portion having lengths of yarn therein which increase gradually from said second predetermined length at said calf portion to said fourth predetermined length at said knee portion, the courses in said third transition portion having lengths of yarn therein which decrease gradually from said fourth predetermined length at said knee portion to said third predetermined length at said lower thigh portion, the variation in the length of yarn in the courses of said tubular body being such that in use on a wearer's leg said tubular body has a circumferential tension which decreases essentially uniformly from said toe end of said foot portion to said upper end of said upper thigh portion, whereby said stocking applies to a wearer's leg a pressure which decreases essentially uniformly from the ball of the wearer's foot to the upper portion of the wearer's thigh.

5. The stocking set forth in claim 4, and further including a relief panel inlaid in said thigh portion of said tubular body along approximately one-half the circumference thereof and disposable in use along the inside of the wearer's thigh.

6. The stocking set forth in claim 4, and further including a seamless welt band integrally knit on said upper end of said tubular body and turned upon itself and integrally knitted with itself to provide a double thickness, each course of said welt band having a first predetermined number of loops therein, every third course of said tubular body having said predetermined number of loops therein and all other courses of said tubular body having one-half said predetermined number of courses therein.

7. A rotary knitted one-piece anti-embolism stocking comprising a seamless tubular body integrally knitted with at least certain of the courses therein of elastomeric yarn so as to impart an elastic character to said body, said body including a foot portion and a boot portion connected to said foot portion, said foot portion having a toe end disposable in use at the ball of the wearer's foot and said boot portion having an upper end disposed away from said foot portion, a seamless toe portion integrally knitted on said toe end of said tubular body and having an open distal end, said distal end of said toe portion being folded back upon itself to form overlapping portions, said overlapping portions being stitched together only along the opposite sides thereof longitudinally of said tubular body, so that said toe portion can be folded to provide both an open toe configuration and a closed toe configuration for said stocking.

8. The stocking set forth in claim 7, wherein said toe portion extends around the entire circumference of said toe end of said foot portion.

9. The stocking set forth in claim 7, wherein said toe portion extends around one-half the circumference of said toe end of said foot portion, said toe portion being folded back along the outer surface of itself.

* * * * *